United States Patent [19]

Marks

[11] Patent Number: 5,149,965
[45] Date of Patent: Sep. 22, 1992

[54] PRECISION RADIOGRAPHY SCALING DEVICE

[75] Inventor: Lloyd A. Marks, Bryn Mawr, Pa.

[73] Assignee: Temple University, Philadelphia, Pa.

[21] Appl. No.: 512,844

[22] Filed: Apr. 23, 1990

[51] Int. Cl.⁵ ............................................. G01B 15/00
[52] U.S. Cl. ................... 250/252.1; 378/207; 378/163
[58] Field of Search ............... 378/207, 162, 163, 164, 378/56, 165; 250/252.1 R

[56] References Cited

U.S. PATENT DOCUMENTS

| | | | |
|---|---|---|---|
| 1,396,920 | 11/1921 | Brostrom | 378/164 |
| 2,650,308 | 8/1953 | Catlin . | |
| 3,217,705 | 11/1965 | Billings | 128/2 |
| 3,687,142 | 8/1972 | Leibinzohn | 128/348 |
| 3,706,883 | 12/1972 | McIntyre | 378/163 |
| 3,770,956 | 11/1973 | Johnson | 378/164 |
| 3,807,390 | 4/1974 | Ostrowski et al. | 350/96 |
| 3,836,776 | 9/1974 | Gullekson | 250/312 |
| 3,887,804 | 6/1975 | Morgan et al. | 250/252.1 |
| 4,005,527 | 2/1977 | Wilson et al. | 250/312 |
| 4,181,859 | 1/1980 | Vitalini | 250/475.1 |
| 4,279,252 | 7/1981 | Martin | 250/491 |
| 4,286,168 | 8/1981 | Carr | 250/510 |
| 4,442,534 | 4/1984 | Haendle et al. | 378/21 |
| 4,459,990 | 7/1984 | Barnea | 128/656 |
| 4,671,291 | 6/1987 | Wilson | 128/658 |
| 4,692,936 | 9/1987 | Billeaudeaux | 378/59 |

OTHER PUBLICATIONS

"Clin Orthop (121)", 83-91, 1976 Clark et al., Improved Methods for Quantitative Radio Graphic Evaluation.

Primary Examiner—Carolyn E. Fields
Assistant Examiner—James Beyer
Attorney, Agent, or Firm—Ratner & Prestia

[57] ABSTRACT

At least one radiopaque sphere of known dimensions with means for positioning same in a radiographic image field and a method for scaling radiographic images including straight AP and lateral views using such a radiopaque sphere.

10 Claims, 2 Drawing Sheets

PRECISION RADIOGRAPHY SCALING DEVICE

FIELD OF THE INVENTION

The invention relates to devices and methods for scaling radiographic images and particularly to devices and methods which facilitate scaling in multiple views.

BACKGROUND OF THE INVENTION

During radiology procedures, and in particular, during angiography, it is often necessary to determine the size of structures or chambers within the body. Because there is an unknown magnification factor relating the actual size of structures to be measured with the images formed on film, it is desirable to have an object of known dimensions with which to compare the body structure.

Catheters, grids of known dimensions and radiopaque cubes of known dimensions are all commonly used as radiography scaling devices, but all have certain inherent disadvantages. If a catheter of known diameter is in the picture, this may be used. However, the catheter must be at the same location as the structure to be imaged, preferably through the structure to be imaged, or an unknown magnification error will result. For more precise measurement, a picture of a grid or a radiopaque cube of known dimensions may be imaged. For the image to be useful, the grid should be the same distance from the imaging beam as the body structure to be measured, and the grid must be positioned so that its known dimension is perpendicular to the imaging beam.

Frequently, it is necessary to image a body structure with views other than straight AP and lateral and often these views are non-orthogonal. If a cube or a grid is used as the reference for a non-orthogonal image, much time is spent tediously positioning the cube or grid so that it is perpendicular to the first image axis, then repositioning it to be perpendicular to the second axis; it is impossible to film the cube or grid with two non-orthogonal cameras simultaneously, as the beams cannot both be perpendicular to the reference object. Furthermore, to obtain a precise reference, it is important for the reference object to be positioned in the same relative position in three dimensional space, with reference to two imaging beams, as the body structure was when the image of the structure was taken. This requires positioning the reference object accurately in order for it to appear in the same place as the body structure on both images simultaneously.

When catheters are used, the catheter diameter is the known image dimension. If a catheter diameter is used as the reference dimension, there may be an inherent inaccuracy unless the catheter is adjacent to or through the body structure being measured, so that it is accurately positioned at the location of interest. Also, because the images of the edges of plastic catheters tend to fade and the catheter casts an image with a small diameter, it may be difficult to precisely measure the catheter diameter. Accordingly, a catheter diameter is an inherently poor reference object.

For all of these reasons, there remains a need for an improved radiography scaling device and method; particularly one which lends itself to image scaling in multiple views.

BRIEF DESCRIPTION OF THE INVENTION

In the present invention, at least one radiopaque sphere is used for scaling radiographic images. The sphere is of known dimensions and includes means for positioning the sphere in any location of the image field. The invention also includes a method for producing multiple images, simultaneously from a radiopaque sphere, and a method of scaling images by comparing the images produced to at least one image of a radiopaque sphere.

DETAILED DESCRIPTION OF THE INVENTION

In medical and veterinary arts, images of internal body structures are produced by electromagnetic radiation using techniques including x-rays and nuclear magnetic resonance. In the present invention, there is provided a device and method for scaling images including straight AP and lateral.

Figure 1:
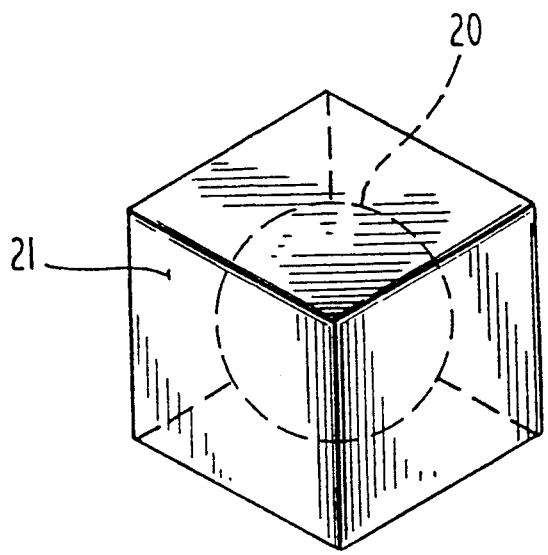
FIG. 1 illustrates an image-scaling sphere encased in a plastic cube.

Referring to FIG. 1, there is shown an embodiment comprising a sphere 20 of steel or some other radiopaque material, and a sphere-encasing cube 21 composed of plastic, such as a Lucite or plexiglas or some other material of differential radiopacity compared to the sphere. Cube 21 may be held in place in the image field by a laboratory clamp, also with a differential radiopacity, or by placing it on surface of the radiography field to be imaged, thus providing a means for positioning cube 21.

Figure 2:
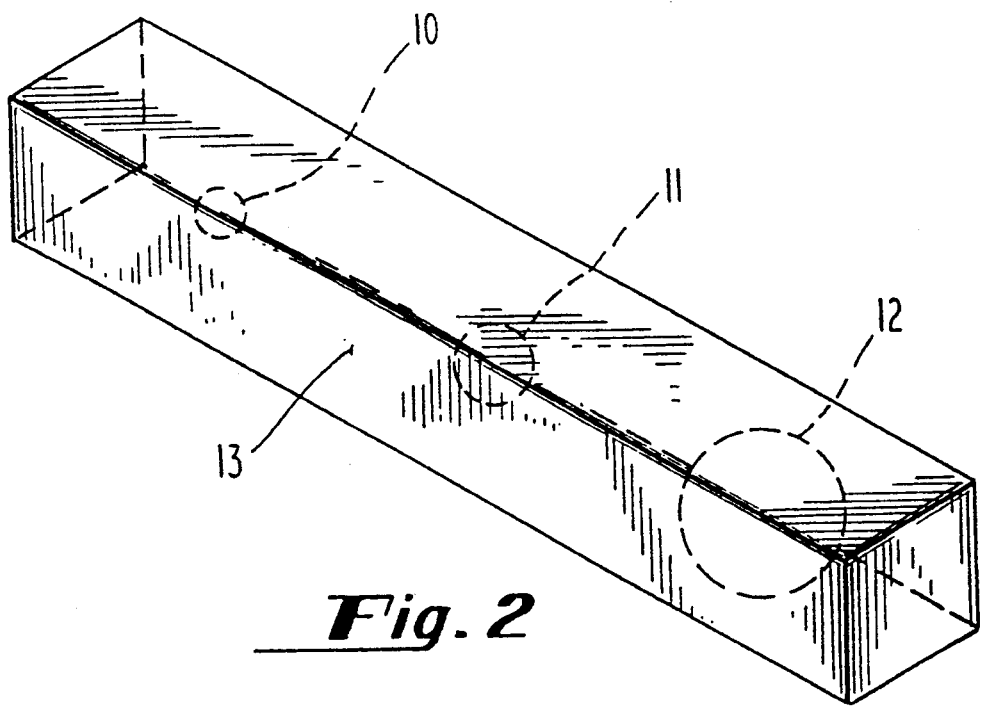
FIG. 2 illustrates a plurality of spheres of different sizes encased in a plastic rectangular solid to dispose the spheres at spaced locations in an image field.

FIG. 2 is an alternative to the embodiment of FIG. 1, and allows spheres to be placed at spaced locations in the image field. In FIG. 2, a plastic rectangular solid 13 encases several radiopaque spheres 10-12 of different sizes, and may be placed along the horizontal or vertical axis of the image field and held in place in the image field. The diameters of the spheres differ from one another by a factor of two, in order to accurately discern the spheres from each other and for use as the scaling reference. The length of the plastic may be equal to the diameter of the image field; however, smaller size variations in the length of the rectangle are also acceptable to account for scaling structures at intermediate points between the center and periphery of the image field.

Figure 3:
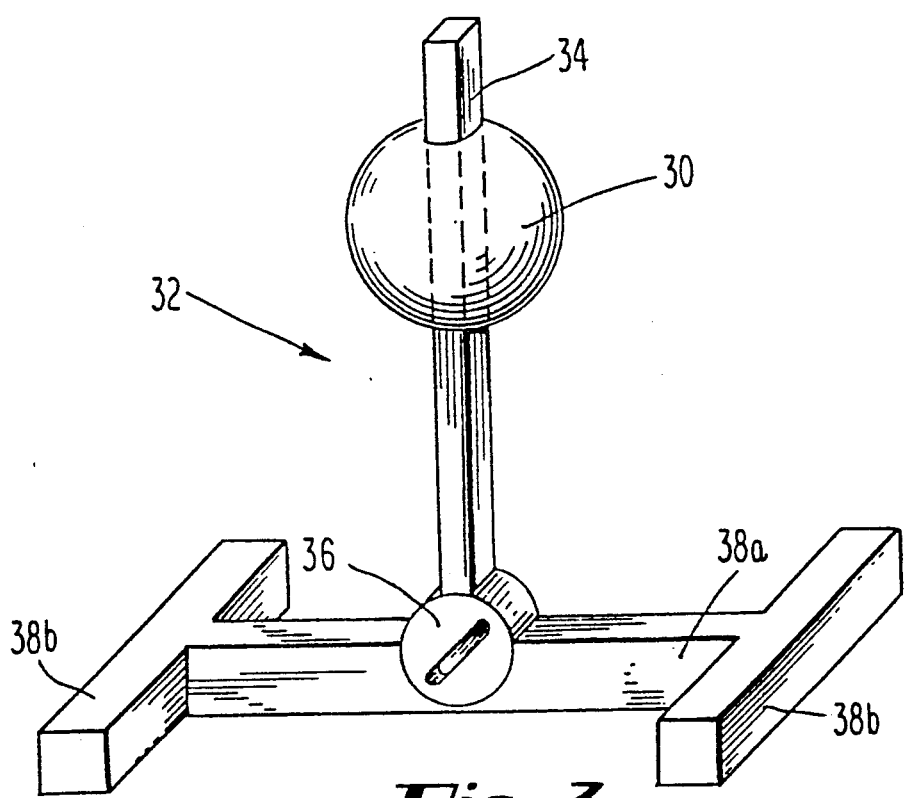
FIG. 3 illustrates a sphere attached to a mechanical device to position the sphere in three dimensions of the image field.

In FIG. 3, there is shown a radiopaque sphere 30, with a three-dimensional positioning device 32. Sphere 30 is slidably mounted on holding arm 34 of positioning device 32. Arm 34 is rotatably mounted through screw wheel 36 to a base member comprised of a cross piece 38a and outboard stabilizer members 38b, which supports arm 34 and prevents collapse. Screw wheel 36, which is frictionally retained in member 38a, and the sliding, but frictionally retained mounting of sphere 30 on arm 34, allows positioning of movable arm 34 and sphere 30 for placement of sphere 30 in essentially any location in the three dimensions of the image field.

Alternatively, sphere 30, as shown in FIG. 3, or a sphere retaining cube (21 in FIG. 1) or a spheres-retaining solid (13 in FIG. 2) may be positioned in a radiographic image field by a holder associated with (either by being attached to or an extension of) one of the other pieces of equipment used in the imaging operation, such as the table supporting the patient or the mechanical means for supporting X-ray equipment by which the images are generated.

The sphere of FIG. 1 may be employed in methods of scaling images by comparing an image of a radiographed object to at least one image of a radiopaque sphere. The sphere is positioned in the same location as the structure to be imaged as seen from two views. This assures that the sphere is placed at the same position in the three dimensional space relative to the imaging beams and the body structure to be imaged. The sphere of FIG. 1 may simply be placed loosely into the retaining cube (or rectangular solid) or may be held therein by a jelled semi-solid. The sphere may also be held in place in the image field by a laboratory clamp with differential radiopacity than the sphere, or by placing it on surface of the radiography field to be imaged.

Alternatively, sphere(s) of FIG. 2-3 may be used. When scaling structures at intermediate points between the center and the periphery of the image field, the device of FIG. 3 may be used as the sphere 30 may be placed at any location in the three dimensions of the image field. When using the embodiment of FIG. 2, the sphere nearest to the location of the imaged structure and identifiable from two different angles, is to be employed as the reference for scaling. Spheres of various sizes may be used in the embodiment of FIG. 3 to accurately identify the sphere used as the scaling reference. Increasing the diameters of the spheres by a factor of two accurately discerns the sphere used as the reference. This method provides an accurate reference for scaling structures by accounting for magnification differences across the image field.

In accordance with a particularly useful application of the present invention, the sphere(s) may also be used as a reference scaling device in a method to produce simultaneous images. In this case, the sphere(s) need not be repositioned for non-simultaneous imaging but serves instead, with a single placement, for scaling reference in simultaneously taken views. Accordingly, two radiographic cameras may be employed at the same time.

Also provided is a method of scaling multiple radiographs of a target structure in an image field. At least two radiographic views are employed, with one or more cameras or other imaging apparatus, for example, having fixed locations, angular orientations and a common image field. The target structure is placed in the image field and images are taken with the radiographic device(s). An object of known spherical dimension is placed in the image field in the same location previously occupied by the target structure, such that the object appears in the same location in at least two views as the structure to be measured, and radiographs are made via the radiographic device(s). Scaling is accomplished by comparing a first dimension to be determined of the target structure to the known dimension of the spherical object made by the same device that produced the image in which the dimension is to be determined.

In the embodiments disclosed above the means for positioning the sphere, such as the cube and laboratory clamp, are disclosed as having differential radiopacity compared to the sphere. Varying the radiopacity is necessary to accurately discern the sphere from the means for positioning as well as for precise scaling. The sphere may be more or less radiopaque than the means for positioning as either would depict the sphere as a discernable scaling reference.

While this invention has been disclosed with reference to a specific embodiment, it is apparent that other embodiments and equivalent variations of this invention may be devised by those skilled in the art without departing from the true spirit and scope of this invention. The appended claims are intended to be construed to include all such embodiments and equivalent variations.

What is claimed is:

1. A method for scaling a radiograph of a target structure within a three dimensional radiographic image field of a radiographic camera comprising placing at least one radiopaque sphere of known dimensions in said three dimensional radiographic image field at a location previously occupied by said target structure when said target structure radiograph was taken and then making a radiograph of said spherical object with said camera, thereafter calculating a first dimension to be determined in said target structure radiograph by comparing said first dimension to the known dimension of said spherical object in the radiograph thereof.

2. The method of claim 1, wherein said at least one sphere is encased in a material of different radiopacity as compared to the sphere.

3. The method of claim 1, wherein a plurality of radiopaque spheres, with unique identifying characteristics, are placed at spaced locations in the image field.

4. The method of claim 3, wherein said unique identifying characteristics of said spheres are differing diameters.

5. The method of claim 4, further including placing at least one sphere in the center of said image field and placing at least one sphere on the periphery of said image field.

6. The method of claim 5, wherein said at least one sphere is encased in a material of different radiopacity as compared to the sphere.

7. The method of claim 4, further including placing at least one sphere in the center of said image field and placing two or more spheres at spaced locations on intermediate points of said image field.

8. The method of claim 7, wherein said at least one sphere is encased in a material of different radiopacity as compared to the sphere.

9. The method of claim 1 wherein said sphere is placed by manipulation of a member associated with a table.

10. A method of scaling radiographs of a target structure in a common three dimensional image field of at least two radiographic devices each having fixed locations and angular orientations, comprising placing a spherical radiopaque object of known spherical dimension in said image field in the same location occupied by said target structure when said target structure radiographs were taken and then making radiographs of said spherical object with said devices, thereafter calculating a first dimension to be determined in one of said target structure radiographs by comparing said first dimension to the known dimension of said spherical object in the radiograph thereof made by the same device which produced the radiograph in which said dimension is to be determined.

* * * * *